United States Patent [19]

Dinkler et al.

[11] Patent Number: 5,529,358
[45] Date of Patent: Jun. 25, 1996

[54] BIFURCATED SURGICAL RETRACTOR

[75] Inventors: Charles Dinkler; Richard B. Budde, both of Cincinnati, Ohio

[73] Assignee: Ohio Medical Instrument Company, Cincinnati, Ohio

[21] Appl. No.: 315,437

[22] Filed: Sep. 30, 1994

[51] Int. Cl.⁶ .................................................. A61B 17/02
[52] U.S. Cl. .................... 600/233; 600/234; 600/229; 403/97
[58] Field of Search ..................... 600/227–233; 602/17, 37; 606/130, 56; 403/83, 84, 85, 87, 91, 96, 97 X, 100, 103

[56] References Cited

U.S. PATENT DOCUMENTS

| Re. 32,021 | 5/1985 | Scott, Jr. ............................. 600/233 |
|---|---|---|
| 1,839,726 | 8/1930 | Arnold ................................. 600/233 |
| 2,384,304 | 8/1944 | Helfrick ............................... 600/233 |
| 3,072,118 | 1/1963 | Standerwick et al. . |
| 3,391,693 | 7/1968 | Georgiade et al. . |
| 4,434,791 | 3/1984 | Darnell ................................ 600/233 |
| 4,457,300 | 7/1984 | Budde . |
| 4,475,550 | 10/1984 | Bremer et al. . |
| 4,617,925 | 10/1986 | Laitinen . |
| 4,682,509 | 7/1987 | Takamiya et al. ..................... 403/97 |
| 4,723,544 | 2/1988 | Moore et al. . |
| 5,178,583 | 1/1993 | Rankin ................................ 403/100 |
| 5,197,965 | 3/1993 | Cherry et al. . |
| 5,217,315 | 6/1993 | Rosane ............................... 403/102 |
| 5,254,079 | 10/1993 | Agbodoe et al. . |
| 5,284,129 | 2/1994 | Agbodoe et al. ..................... 128/20 |

FOREIGN PATENT DOCUMENTS 0089099  9/1983  European Pat. Off. ........ A61B 17/02

*Primary Examiner*—Richard J. Apley
*Assistant Examiner*—Kelly McGlashen
*Attorney, Agent, or Firm*—Wood, Herron & Evans

[57] ABSTRACT

A halo style surgical retractor having fixed and movable curvilinear members each of which has an outwardly directed retractor channel extending over the full length of the member. A support arm is attached to the fixed member to hold the fixed member in a desired fixed, but adjustable position. The ends of fixed and movable members are coupled together so that, first, when the members are brought into a generally coplanar relationship, there is an uninterrupted and continuous retractor holder path around the combined length of the fixed and movable members. Second, the couplings permit the movable member to pivot to a position directly above and overlaying with the fixed retractor member, that is, a position in which the movable retractor member is in a plane directly above and generally parallel to the plane of the fixed retractor member.

14 Claims, 2 Drawing Sheets

5,529,358

BIFURCATED SURGICAL RETRACTOR

FIELD OF THE INVENTION

This invention relates generally to the field of surgical instruments, and more particularly, to apparatus for holding bodily tissues, membranes, and vessels, retracted during cranial surgery.

BACKGROUND OF THE INVENTION

Surgical retractors for holding tissues at the edge of a surgical incision, or wound, away from the field of an operation have been in use for years. A halo style annular retractor is disclosed in the Budde U.S. Pat. No. 4,457,300, assigned to the assignee of the present invention. The retractor is comprised of a ring having a circumferential channel on the outside periphery of the ring. The channel is adapted to receive and support a retractor holder, which in turn supports a retractor blade or other tool. The retractor holder can be moved continuously through a 360° path around the retractor ring.

In an embodiment disclosed in the Agbodoe, et al. U.S. Pat. No. 5,284,129, a halo style retractor is split into two semicircular ring sections which are pivotally connected together at their ends. One of the semicircular ring sections swivels with respect to the other ring section which is supported in a fixed position. The swiveling ring section is unlocked and relocked into a desired position by means of a screw clamp mechanism. The screw clamp mechanism may be disassembled to remove the swiveling ring section from the fixed ring section. The construction of the Agbodoe '129 reference has several disadvantages. First, the pivot joints at the ends of the ring sections interrupt the path of movement, and retractor holders cannot be positioned at or slid past the ends of the ring sections. Consequently, to move a retractor holder from one ring section to the other, the retractor holder must be physically removed from the one ring section and then remounted to the other ring section. That requirement has the disadvantages of consuming time during a surgical procedure, and of exposing the retractor to mishandling, being dropped, etc.

With the design in the Agbodoe '129 patent, the knob for locking the movable retractor in a particular position is located on the outer circumference of the retractor ring. In addition, the locking knobs on the retractor holders are also located on an outwardly directed surface of the retractor holders. Consequently, if the retractor holders are located at the ends of the semi-circular ring sections, the locking knob for the retractor holder is adjacent the locking knob for the retractor ring with the further disadvantage that there is interference in the manipulation and operation of either one of the two locking knobs.

The interruption of the circumferential retractor holder path by the pivot joints on opposing sides of the retractor ring results in the ring sections interfering with each other when one attempts to fold the moveable ring section up and over the fixed ring section. Therefore, in order to obtain greater access to the surgical field, the swiveling semicircular ring section must be disassembled and physically removed from the retractor. That process has the disadvantage of requiring surgical personnel to engage in a time-consuming disassembly process, and in addition, keep track of the loose parts which result from the disassembly process.

SUMMARY OF THE INVENTION

To overcome the disadvantages described above and to provide a more versatile retractor system, the present invention provides a bifurcated surgical retractor which has a continuous curvilinear retractor holder path around the periphery of both retractor members when the bifurcated retractor members are in a generally coplanar position. Further, the bifurcated surgical retractor of the present invention provides greater access to the surgical field by simply folding the swiveling retractor member into juxtaposition with the fixed member. Therefore, the invention is suited for a wider range of cranial surgical procedures, and is especially useful in those procedures in which a continuous retractor holder path around both retractor members is useful, or which require greater access to the surgical field, or which require that retractor holders be located at the ends of the retractor members.

According to the principles of the present invention and in accordance with the described embodiments, a halo style surgical retractor has fixed and movable curvilinear members each of which has an outwardly directed retractor channel extending over the full length of the member. A support arm is attached to the fixed member to hold the fixed member in a desired fixed, but adjustable position. The retractor includes means for coupling the ends of the fixed and movable members together so that, when the members are brought into a generally coplanar relationship, there is an uninterrupted and continuous retractor holder path around the combined periphery of the fixed and movable members. Therefore, when the retractor members are coplanar, the present invention has the advantage of allowing a retractor holder to be moved continuously around the periphery of the fixed and movable retractor members without having to be removed and reattached. The present invention has a further advantage of allowing retractor holders to be positioned at the ends of the curvilinear members.

In a further embodiment of the invention, the coupling between the movable and fixed retractor members has a hinge permitting the movable member to pivot a position directly above and overlaying with the fixed retractor member, that is, a position in which the movable retractor member is in a plane directly above and generally parallel to the plane of the fixed retractor member. Consequently, the construction of the present invention has the advantage of permitting greater access to the surgical field simply by pivoting the movable retractor member up, over, and on top of the fixed retractor member. There is a further advantage in that no parts or components have to be disassembled or removed to pivot the movable member to that overlying position. The overlying relationship between the movable and fixed members also has the advantage of permitting more retractor holders to be mounted on the retractor. The juxtaposed side-by-side relationship of the retractor members has the further advantage of allowing retractor holders to enter the channel from several different entry points. Further, the interior location of the clamp knob for the retractor advantageously eliminates interference with the locking knobs on the retractor holders.

In a further embodiment of the invention, the clamping mechanism associated with the coupling between the fixed and movable retractor members is manually operable from the inside of the fixed and movable retractor members.

In a further embodiment of the invention, the fixed and movable retractor members are coupled by two intervening clamping links which are pivotally connected to, and join, the ends of the fixed and movable retractor members to provide two generally parallel axes of rotation for the movable retractor member. In that embodiment, each end of both the fixed and movable retractor members has a pivot pin connected thereto which is directed inwardly and extends a predetermined distance beyond the inner surface of the members. A clamping link is slidably mounted on the pivot pins, thereby connecting the ends of the fixed and movable retractor members together. A fixed link is fastened to the ends of the pivot pins and is parallel to the clamping link. An actuator is mounted to the fixed link and connected to the movable link. Operating the actuator in one direction moves the clamping link into engagement with the respective ends of the movable and fixed retractor members to clamp the ends of the members together, thereby securing the movable retractor member in a predetermined orientation with respect to the fixed retractor member. The clamping link allows the ends of the movable clamping member to move to different spatial positions with respect to the ends of the fixed clamping member with the advantage that the movable member may be moved through a greater range of useful positions with respect to the fixed member.

These and other objects and advantages of the present invention will become more readily apparent during the following detailed description, together with the drawings herein.

DETAILED DESCRIPTION OF THE INVENTION

Figure 1:
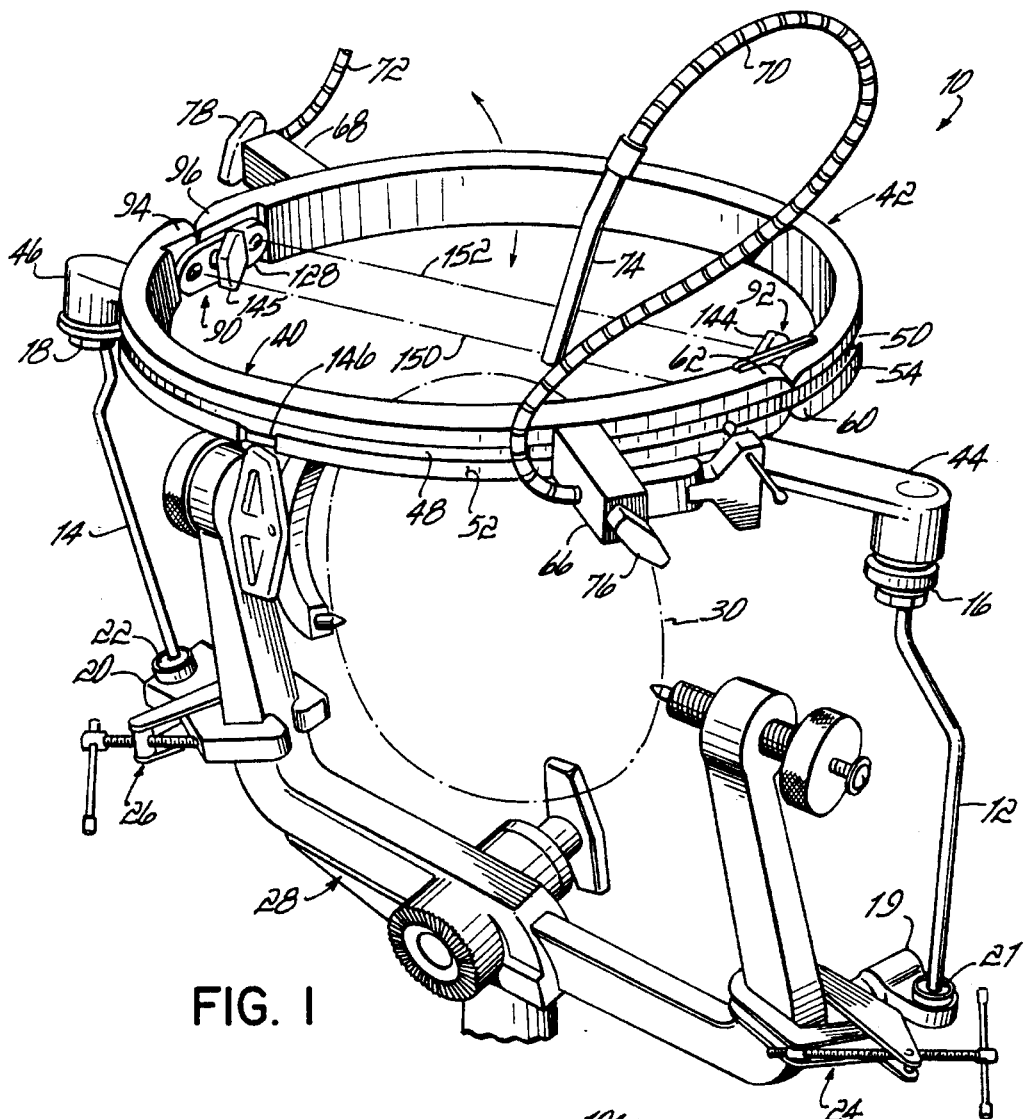
FIG. 1 is a respective view illustrating the retractor of the present invention as it is mounted on an associated skull clamp.
Figure 2:
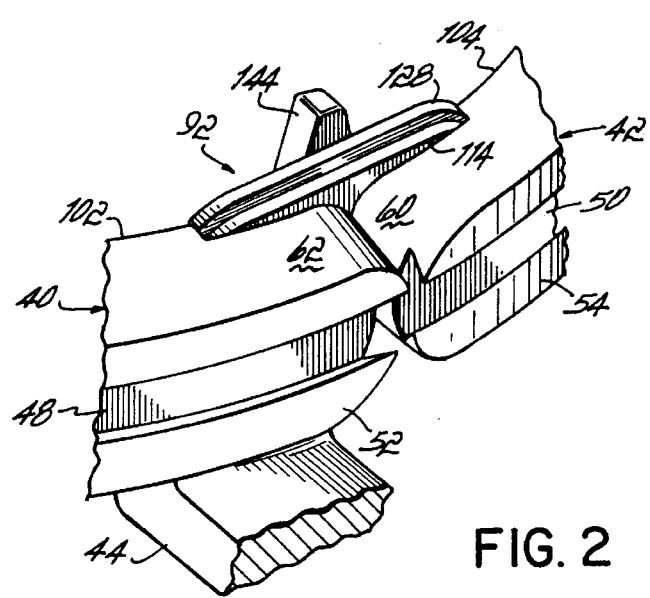
FIG. 2 is an enlarged view of abutting ends of one side of the retractor and illustrates the continuity of the retractor holder path between the two curvilinear sections.

Referring to FIG. 1 the surgical retractor 10 of the present invention is shown mounted on support rods 12, 14 which are pivotally connected to the retractor 10 by respective ball and socket joints 16, 18. The other end of the support rods 12, 14 are pivotally connected into lower support brackets 19, 20 by means of respective ball and socket joints 21, 22. The lower support brackets are coupled to respective kant twist clamps 24, 26 which in turn are mounted to the legs of a skull clamp 28 supporting a patient's head 30 shown in phantom.

The ball and socket joints 16, 18, 21, 22 permit the retractor 10 to be oriented with respect to a desired plane at a desired location with respect to the head 30. The retractor 10 includes a fixed curvilinear member 40 and a moveable curvilinear member 42. The fixed member 40 is connected to first ends of two L-shaped opposed brackets, or supports, 44, 46 which extend radially from the ends of the fixed member 40. The distal ends of the brackets 44, 46 are coupled by the ball and socket joints 16, 18 to the upper ends of the support arms 12, 14. Therefore, the fixed curvilinear member 40 may be manipulated and fixed in the desired position and orientation with respect to a patient's head 30.

The fixed and moveable members 40, 42 have respective slots, or channels, 48, 50 which are located on respective outer directed surfaces, that is, outside surfaces, 52, 54. The slots 48, 50 extend over the full length of the outside surfaces 52, 54 and intersect the surfaces on the ends of the members 40, 42. The slots, or channels, 48, 50 may be of any shape. However, preferably they have the well known dovetail shape and are sized to receive mating dovetail projections (not shown) extending from one end of the retractor arm holders 66, 68. Flexible retractor arms 70, 72 have one end attached to the respective retractor arm holders 66, 68. A spatula-like retractor blade 74 or other device for retracting tissue and other detail is connected to the other end of the retractor arm 70. The knobs 76, 78 are used to loosen the clamps locking the respective retractor arm holders, 66, 68 in position. The retractor arm holders 66, 68 may then be moved to any peripheral position on the fixed and moveable curvilinear members 40, 42 including positions that are immediately at the ends of the members 40, 42 or a position that is between and extends across the ends of the members 40, 42. When the curvilinear members 40, 42 are in a generally coplanar position, the channels 48, 50 are end-to-end such that they form a continuous and uninterrupted 360° path for the retractor arm holders 66, 68. Therefore, the retractor arm holders 66, 68 can be slidingly moved through the slot 48 of fixed member 40 directly into dovetail slot 50 of moveable member 42 without having to remove the retractor arm holders from the retractor 10. Further, the retractor arm holders can be slid from the slot 48 to the slot 50 and visa-versa even when the moveable member 42 is angled with respect to the plane of the fixed member 40 by an angle of inclination of up to plus or minus 10°. When the retractor arm holders 66, 68 are moved to the desired position, the knobs 76, 78 are then used to tighten the clamp securing the retractor arm holder 66, 68 in the dovetail slots 48, 50 at the desired positions.

The moveable curvilinear member 42 may be pivoted with respect to the fixed curvilinear member 40 and locked into any orientation with respect to the fixed member 40 by means of clamps, or connectors, 90, 92. The clamp mechanisms 90 and 92 are identical in construction, and the clamp mechanism 90 is shown in detail in FIGS. 3 and 4. First ends 94, 96 of the respective members 40, 42 contain shafts 98, 100 which are attached to and project inwardly from the inside surfaces 102 and 104 of the respective members 40, 42. The shafts 98, 100 are rigid posts which function as pivot pins and provide axes of motion for the clamp 90 about which the moveable member 42 may be rotated. The inside surfaces 102, 104 of members 94, 96 contain respective notches, or recesses 106, 108. First and second locking members, for example, toothed rings or sunburst clamps, 110, 112 have respective first and second engagement surfaces, or toothed rings, and are connected within the respective notches 106, 108. The toothed rings 110, 112 have central bores 116 through which the pivot pins 98, 100 extend. The pivot pins 98, 100 may be threaded into the respective members 40, 42. Alternatively, the pins 98, 100 may be rigidly secured to the members 40, 42 by adhesive or by driving the pins into a bore sized to provide an interference fit. Any known method that fixes the pins 98, 100 with respect to the members 40, 42 may be used.

The clamp mechanism 90 further includes a clamping link 114 having two through-bores 116 which are positioned and sized so that the clamping link 114 can be mounted on and freely slide over the projecting shafts 98, 100. The clamping link 114 further includes a third toothed ring or starburst clamp 118 and a fourth toothed ring, or starburst clamp 120 which are positioned on the clamping link 114 to be opposite from and mate with the first and second toothed rings 110, 112, respectively. The members 40, 42 have counter-bores 122 concentric with the through bores 116; and the clamping link 114 has mating and opposed counter bores 124. Wave washers or springs 126 are located on the shafts 98, 100 within the counter bores 122, 124. The wave washers or springs 126 apply a bias or force tending to separate the first and third toothed rings 110, 118, and the second and the fourth toothed rings 112, 120.

The clamp 90 also includes a fixed link 128 which is attached to the distal or outermost ends 130 of the shafts 98, 100. The fixed link 128 may be connected to the shafts 98, 100 by welding, adhesives or other known mechanisms. In the illustrated embodiment, the ends 130 of the shafts 98, 100 are manufactured to have a smaller diameter shaft 132 on their ends. The fixed link 128 contains throughbores 134 which are sized to receive the smaller diameter shafts 132. When the fixed link 128 is mounted on the smaller diameter shafts 132, the fixed link bears against a stop surface or shoulder 136 which maintains the fixed link 128 a predetermined distance from the inside surfaces 102, 104 of the members 40, 42. Screws 138 are threaded into the ends 130 of the shafts 98, 100 to rigidly secure the fixed link 128 to the ends 130 of the shafts 98, 100. The fixed link 128 also has a threaded hole 140 which is preferably centrally located on the fixed link 128. The threaded hole 140 receives a threaded shaft 142 which is connected at one end to a knob 145.

Figure 4:
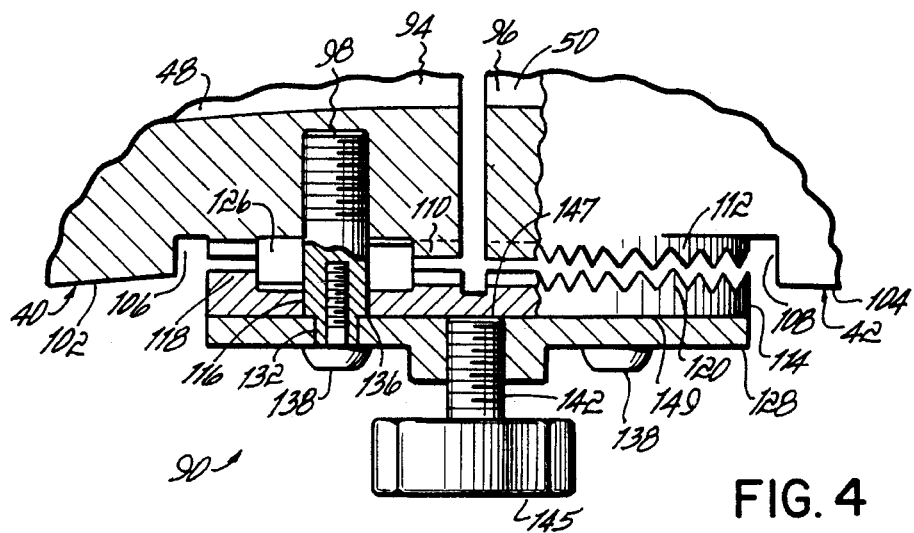
FIG. 4 is a partial cross-sectional view illustrating the clamp in its open position which permits the moveable member to pivot with respect to the fixed member.

In use, the knobs 144, 145 are rotated in the first rotational direction, for example, a counterclockwise direction, to unlock the movable member 42 from the fixed member 40. As shown in FIG. 4, rotating the knob 145 in the counterclockwise direction will move the knob 145 and its connecting screw 142 in a generally vertically downward direction. The biasing springs 126 are effective to push against the clamping link 114 in a direction toward the center of the retractor thereby disengaging the first and third toothed rings 110, 118 and the second and fourth toothed rings 112, 120. When both of the knobs, 144, 145 have been loosened, the first and second ends 60, 96 of the movable member 42 which are respectively proximate the first and second ends 62, 94 of the fixed member 40 are free to pivot with respect to the fixed member 40. Referring to FIG. 1, the moveable member 42 rotates with respect to a first axis of rotation 152 that extends between the ends 60, 96 of the moveable member 42 and passes centrally through the pins 100. Therefore, the moveable member 42 is pivotally rotated about an axis of rotation 152 with respect to the pins 100. Further, the movable member 42 is free to rotate with respect to the pivot pins 98 which are located in the opposite ends 94, 62 of the fixed member 40. Therefore, the pins 98 define a second axis of rotation 150 that extends centrally through the pins 98 between the ends 94, 62 of the fixed member 40.

Figure 5:
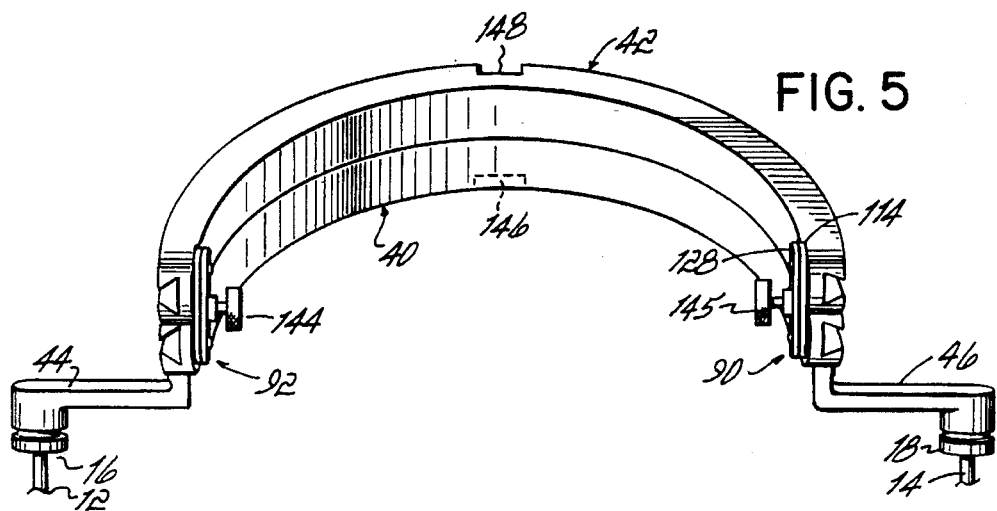
FIG. 5 is a perspective view illustrating how the moveable curvilinear section folds up on top of and over the fixed section.

If it is desired to have greater access to the surgical field, the moveable member 42 is moved up and over the fixed member 40 to a position where the moveable member 42 lies directly on top of the fixed member 40 as shown in FIG. 5. In that position, the members 40, 42 and their respective channels 48, 50, are approximately parallel; and a plane longitudinally bisecting, that is, defined by the curvilinear longitudinal centerline, of the moveable member 42 is approximately parallel to a plane longitudinally bisecting and containing the curvilinear longitudinal centerline of the fixed member 40. When the retractor members are in that folded and generally parallel position, retractor holders may be inserted in the retractor holder paths 48, 50 from any one of six different locations. The retractor holders may be inserted through the ends 60, 62, 94, 96 of the retractor members 40, 42 and may also be inserted through the entry slots 146, 148 which are located midway around the length of each of the retractor members 40, 42 as shown in FIGS. 1 and 5. If from the position illustrated in FIG. 5, the movable member is rotated 180°, the movable member 42 will lie in a plane parallel to but offset from the plane of the fixed retractor 40. The magnitude of the offset between the two planes is determined by the distance between the shafts 98, 100.

Figure 3:
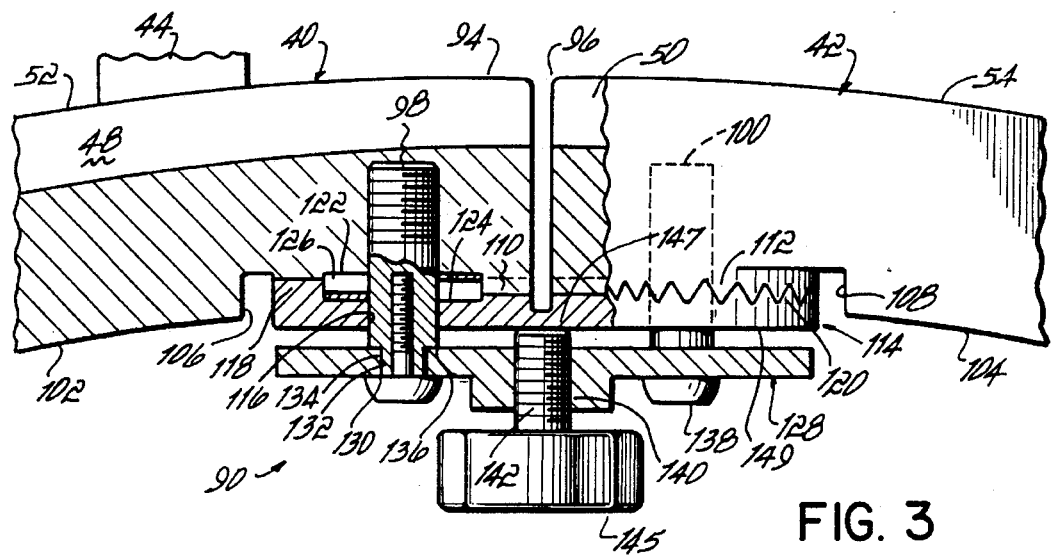
FIG. 3 is a partial cross-sectional view illustrating the clamp in its closed position locking the curvilinear members together.

From that folded position, the movable member may be pivoted through more than 270° of rotation until its motion is blocked by the support brackets 44, 46. After the moveable member 42 has been manipulated to a desired position and orientation, the knobs 144, 145 are rotated in an opposite direction, for example, a clockwise direction. Referring to FIG. 3, rotation of the knob 145 will move the threaded shaft 142 and connecting knob 145 in a vertically upward direction as viewed in FIG. 3. The other end 147 of the threaded shaft 142 bears against an outer surface 149 of the clamping link 114. Therefore, as the knob 145 is twisted clockwise thereby moving the knob and its connecting shaft 142 in the vertically upward direction, the end 147 of the screw 142 contacts the clamping link 114 and also moves it in a vertically upward direction. In that process, the first and third toothed rings 110, 118 and the second and fourth toothed rings 112, 120 matingly engage thereby causing a rigid connection therebetween. Consequently, the clamp mechanisms 90, 92 are effective to secure the clamping link 114 to the ends 94, 96 of the members 40, 42 thereby locking the members in a rigid and fixed position with respect to each other.

While the invention has been set forth by a description of the embodiment in considerable detail, it is not intended to restrict or in any limit the claims to such detail. Additional advantages and modifications will readily appear to those who are skilled in the art. For example, the threaded shafts 142 connected to the knobs 144, 145 may be rotatably coupled to the clamping links 114. Consequently, the clamping links 114 will follow the linear motion of the threaded shaft 142 as the knobs 144, 145 are rotated; and therefore, the wave washers or biasing springs 126 may be omitted from the clamp 90. Accordingly, departures may be made from the details described herein without departing from the spirit and scope of the invention.

What is claimed is:

1. A surgical retractor frame for supporting a retractor arm holder, the retractor frame comprising:

a curvilinear fixed member having
      first and second ends, and
      a first path adapted to receive a retractor arm holder and extending around a length of the fixed member;

a support connected to the fixed member for holding the fixed member in a desired position;

a curvilinear movable member having
      first and second ends, and
      a second path adapted to receive a retractor arm holder and extending around a length of the movable member; and connectors coupled between the respective first ends and the respective second ends of the movable and the fixed members for providing rotation of the movable member to a first position substantially overlapping and parallel with the fixed member.

2. The surgical retractor of claim 1 wherein each of the connectors comprises:

a first clamp pivotally connected between the first ends of the fixed and movable members; and a second clamp pivotally connected between second ends of the fixed and movable members.

3. The surgical retractor of claim 2 wherein the first and second clamps include first and second links, respectively, connected between the ends of the fixed and movable members.

4. The surgical retractor of claim 1 wherein the first position of the movable member is in a plane substantially parallel to but offset from a plane defined by a curvilinear longitudinal centerline of the fixed member.

5. The surgical retractor of claim 1 wherein the curvilinear fixed and movable members are substantially semicircular in shape.

6. The surgical retractor of claim 1 wherein the first and second paths are channels in outside surfaces of the fixed and movable members, respectively.

7. The surgical retractor of claim 1 wherein the connector permits motion of the movable member to a second position generally coplanar with the fixed member and providing an uninterrupted 360° path for the retractor arm holder through the first and second paths of the respective fixed and movable members.

8. The surgical retractor of claim 1 wherein the connector provides two substantially parallel axes of rotation about which the movable member can be rotated.

9. A surgical retractor frame for supporting a retractor arm holder, the retractor frame comprising:

a curvilinear fixed member having
first and second ends, and
a first path adapted to receive a retractor arm holder and extending around a length of the fixed member;

a curvilinear movable member having
first and second ends, and
a second path adapted to receive a retractor arm holder and extending around a length of the movable member so as to be substantially continuous with the first path;

a support connected to the fixed member to hold the fixed member in a desired position;

at least one retractor arm holder slidably mounted in one of the first and second channels; and connectors coupled between the respective first ends and the respective second ends of the movable and the fixed members for providing motion of the movable member to a position generally coplaner with the fixed member and providing an uninterrupted 360° path for the retractor arm holder through the first and second paths of the respective fixed and movable members.

10. A surgical retractor frame for supporting a retractor arm holder, the retractor frame comprising:

a curvilinear fixed member having
first and second ends, and
a first path adapted to receive a retractor arm holder and extending around a length of the fixed member;

a curvilinear movable member having
first and second ends, and
a second path adapted to receive a retractor arm holder and extending around a length of the movable member;

a support connected to the fixed member to hold the fixed member in a desired position; and connectors coupled between the respective first ends and the respective second ends of the movable and the fixed members for providing two substantially parallel axes of rotation about which the movable member can be rotated.

11. The surgical retractor of claim 10 wherein the two axes of rotation further comprise:

a first axis of rotation extending generally between the first end and the second end of the fixed member; and a second axis of rotation extending generally between the first end and the second end of the movable member.

12. A surgical retractor frame for supporting a retractor arm holder, the retractor frame comprising:

a curvilinear fixed member having
first and second ends, and
a first adapted to receive a retractor arm holder and extending around a length of the fixed member;

a curvilinear movable member having
first and second ends, and
a second path adapted to receive a retractor arm holder and extending around a length of the movable member so as to be substantially continuous with the first path;

a support connected to the fixed member to hold the fixed member in a desired position; and clamps for coupling the first and the second ends of movable member to the first and the second ends, respectively, of the fixed member, each of the clamps including a manually operable knob mounted on an inside surface of the respective fixed and movable members for locking and unlocking the clamp and providing an uninterrupted path around the outside surface, thereby locking and releasing, respectively, the movable member with respect to the fixed member.

13. A surgical retractor frame for support in a retractor arm holder, the retractor frame comprising:

a generally semicircular fixed member having
first and second ends, and
a first channel extending around a circumference of the fixed member and adapted to receive a retractor arm holder;

a generally semicircular movable member having
first and second ends located proximate the first and second ends, respectively, of the fixed member, and
a second channel extending around a circumference of the movable member and adapted to receive the retractor arm holder, the fixed and movable members having a known relative position permitting the retractor arm holder to he moved continuously through the first and second channels;

a support connected to the fixed member to hold the fixed member in a desired position;

a first pair of locking members, one member of the first pair of locking members being connected to the first end of the fixed member, and the other member of the pair of members being connected to the first end of the movable member;

two pins, each of the pins having
one end rigidly connected to the one of the proximate first ends of the one of the fixed and the movable members, and
an opposite end directed inwardly toward one of the second ends of the one of the fixed and the movable members, the opposite end of the pin extending a predetermined distance beyond one of the pair of locking members;

a clamping link slidably mounted on the two pins, the clamping link having a second pair of locking members located directly opposite the first pair of locking members, the first end of the movable member being pivotable with respect to the clamping link about an axis, of rotation defined by a first pin connected to the first end of the movable member, and further, the clamping link being pivotable with respect to the fixed member about an axis of rotation defined by a second pin connected to the fixed member;

a fixed link connected to the opposite ends of the pins; and an actuating shaft coupled to and moving with respect to the fixed link, the actuating shaft having one end rotatably connected to the clamping link, whereby moving the actuating shaft in a first direction moves the clamping link toward the first ends of the fixed and the movable members, thereby engaging the second pair locking members with the first pair of locking members and rigidly fixing the position of the first end of the movable member with respect to the first end of the fixed member, and whereby further, moving the actuating shaft in a second direction moves the clamping link away from the first ends of the fixed and the movable members, thereby disengaging the second pair of locking members from the first pair of locking members and allowing the movable member to move with respect to the fixed member.

14. A surgical retractor frame for supporting a retractor arm holder, the retractor frame comprising:

a generally semicircular fixed member having
  a first end,
  a second end,
  a generally semicircular first channel extending around a length of the fixed member and adapted to receive a retractor arm holder,
  a first element connected to the first end of the fixed member, the first element having first engagement surface directed inwardly toward the second end of the fixed member, and
  a first pin having
    one end rigidly connected to the first end of the fixed member, and
    an opposite end directed inwardly toward the second end of the fixed member, the opposite end of the first pin extending a predetermined distance beyond the first engagement surface;

a generally semicircular movable member having
  a first end,
  a second end,
  a generally semicircular second channel extending around a length of the movable member and adapted to receive the retractor arm holder, the fixed and movable members having a known relative position permitting the retractor arm holder to be moved continuously through the first and second channels,
  a second element connected if proximate to the first end of the movable member, the second element having second engagement surface directed inwardly toward the second end of the movable member, and
  a second pin having
    one end rigidly connected to the first end of the movable member, and
    an opposite end directed inwardly toward the second end of the movable member, the opposite end of the second pin extending a predetermined distance beyond the second engagement surface;

a support connected to the fixed member to hold the fixed member in a desired position;

at least one retractor arm holder slidably mounted in one of the first and second channels;

a retractor blade attached to the retractor holder;

a clamping link slidably mounted on the two pins, the clamping link having third and fourth elements connected to the clamping link, the third and fourth elements having respective third and fourth engagement surfaces directed toward the respective first and second engagement surfaces whereby the first end of the movable link member pivots with respect to the clamping link about an axis of rotation defined by the second pin connected to the first end of the movable member, and whereby further, the clamping link pivots with respect to the fixed member about an axis of rotation defined by the first pin connected to the fixed member;

a fixed link connected to the opposite ends of the pins; and an actuating shaft having one end threaded through the fixed link and rotatably coupled to the clamping link, the actuating shaft having a knob on a second end adapted to be manually twisted, whereby twisting the knob in a first angular direction moves the actuating shaft and the clamping link toward the first ends of the fixed and the movable members, thereby simultaneously meshing the third and the fourth engagement surfaces of the respective third and the fourth elements with the first and the second engagement surfaces of the respective first and the second elements, thereby clamping the position of the first end of the movable member with respect to the first end of the fixed member, and whereby further, twisting the knob in a second angular direction opposite the first angular direction moves the actuating shaft and clamping link away from the first ends of the fixed and the movable members, thereby simultaneously disengaging the third and the fourth engagement surfaces of the respective third and fourth elements from the first and the second engagement surfaces of the respective first and the second elements, thereby unclamping the movable member with respect to the fixed member.

* * * * *

UNITED STATES PATENT AND TRADEMARK OFFICE
CERTIFICATE OF CORRECTION

PATENT NO. : 5,529,358
DATED : June 25, 1996
INVENTOR(S) : Charles Dinkler, et al.

It is certified that error appears in the above-indentified patent and that said Letters Patent is hereby corrected as shown below:

In the claims:

Column 8, line 14, after first, insert --path--.

Column 8, line 33, delete "support in" and insert --supporting--.

Column 8, line 47, delete "he" and insert --be--.

Column 9, line 3, delete ",".

Column 10, line 1, delete "if proximate".

Column 10, line 23, delete "link".

Signed and Sealed this

Twenty-second Day of July, 1997

Attest:

BRUCE LEHMAN

Attesting Officer

Commissioner of Patents and Trademarks